(12) United States Patent
Horiuchi et al.

(10) Patent No.: US 6,310,065 B1
(45) Date of Patent: Oct. 30, 2001

(54) PYRIDAZINONE HYDROCHLORIDE COMPOUND AND METHOD FOR PRODUCING THE SAME

(75) Inventors: Takashi Horiuchi; Sachiko Matsumoto; Hiroo Matsumoto, all of Chiba; Minako Kamikawaji, Tokyo, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/646,127

(22) PCT Filed: Mar. 30, 1999

(86) PCT No.: PCT/JP99/01629

§ 371 Date: Sep. 28, 2000

§ 102(e) Date: Sep. 28, 2000

(87) PCT Pub. No.: WO99/50248

PCT Pub. Date: Oct. 7, 1999

(30) Foreign Application Priority Data

Mar. 31, 1998 (JP) .................................................. 10-085920

(51) Int. Cl.$^7$ ........................ A61K 31/501; C07D 403/12
(52) U.S. Cl. ...................................... 514/252.02; 544/238
(58) Field of Search ........................ 544/238; 514/252.02

(56) References Cited

FOREIGN PATENT DOCUMENTS

95/01343 * 1/1995 (WO) .

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention relates to a 3/2-hydrochloride of 4-chloro-5-[3-(4-benzylpiperazin-1-yl) carbonylmethoxy-4-methoxybenzylamino]-3(2H)-pyridazinone, and also relates to a method for producing the 3/2-hydrochloride of 4-chloro-5-[3-(4-benzylpiperazin-1-yl)carbonylmethoxy-4-methoxy-4-methoxybenzylamino]-3(2H)-pyridazinone which comprises crystallizing in an alcohol type solvent or an alcohol type-ester type mixture solvent in the presence of hydrogen chloride and water.

13 Claims, 1 Drawing Sheet

PYRIDAZINONE HYDROCHLORIDE COMPOUND AND METHOD FOR PRODUCING THE SAME

TECHNICAL FIELD

The present invention relates to a 3/2-hydrochloride of a pyridazinone compound having a bronchodilation function, an antiallergy function and/or an antiplatelet function, and a method for producing the same.

BACKGROUND ART

A pyridazinone compound of the formula (1), i.e. 4-chloro-5-[3-(4-benzylpiperazin-1-yl) carbonylmethoxy-4-methoxybenzylamino]-3(2H)-pyridazinone is disclosed in WO95/01343 laid open on Jan. 12, 1995 and JP-A-8-041033 laid open on Feb. 13, 1996, and is a compound useful as a pharmaceutical product having a bronchodilation function, an antiallergy function or an antiplatelet function.

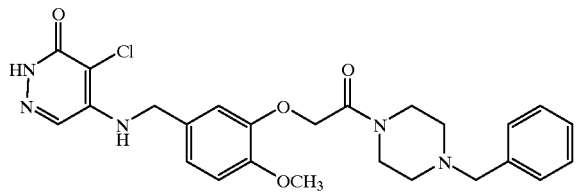

(1)

The above patent publications disclose a hydrochloride of the pyridazinone compound (1) and a method for producing the same, and a 2-hydrochloride (see Reference Example 1) obtained by the above preparation method has an excellent pharmaceutical effect. However, the 2-hydrochloride is highly hygroscopic and is easily decomposed and is rapidly decomposed in a methanol solvent. Thus, the 2-hydrochloride is unstable, and is therefore not suitable as a starting material for a pharmaceutical product.

DISCLOSURE OF THE INVENTION

In order to solve the above-mentioned problems, the present inventors have intensively studied, and have discovered that the pyridazinone compound (1) takes a 3/2-hydrochloride form (2) in addition to a 2-hydrochloride form. Further, as proved by the following Test Example 1, the present inventors have discovered that the pyridazinone compound (1) in the form of 3/2-hydrochloride (2) is clearly excellent in hygroscopicity and stability.

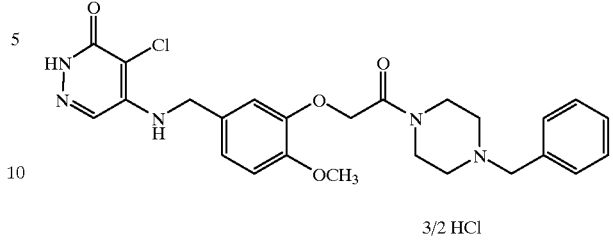

(2)

3/2 HCl

Further, the compound (1) and its 3/2-hydrochloride (2) were compared with regard to biological dynamics in a dog. As this result, it was found that as compared with the compound (1), the 3/2-hydrochloride has 5.4 times higher maximum concentration in blood (Cmax) and is 2.3 times more preferable in respect of area under the curve (AUC) of time-concentration in blood (0-∞). Thus, it was proved that the 3/2-hydrochloride (2) is excellent as a starting material for a pharmaceutical product as compared with the compound (1). Result: (10 mg/kg oral administration by capsules)

TABLE 1

| Compound | Cmax (ng/ml) | AUC (0–∞) (ng/ml · hr) |
| --- | --- | --- |
| 1 | 249.7 | 844.3 |
| 2 | 1349.0 | 1998.3 |

Further, it was found that the 3/2-hydrochloride achieves a pharmaceutical effect equivalent to that of 2-hydrochloride, and it was therefore confirmed that the 3/2-hydrochloride has a satisfactory applicability as a starting material for a pharmaceutical product. The present invention has been completed on the basis of the above-mentioned discovery.

On the other hand, as shown in Reference Example 3, a method for producing a 1-hydrochloride has been discovered. However, this compound is hardly decomposed, but has a high hygroscopicity, and its crystal is easily electrostatically charged, and this compound is poor in solubility and is colored by light. Thus, in view of its physical properties, this compound is not suitable as a starting material for a pharmaceutical product. Still further, according to powder X-ray diffraction analysis, it was proved that the 3/2-hydrochloride is not a mixture of 2-hydrochloride and 1-hydrochloride (see Test Example 2 and FIG. 1 showing powder X-ray diffraction data).

Thus, the present invention relates to a 3/2-hydrochloride (2) of a pyridazinone compound (1) and a method for producing the same.

The method for producing the 3/2-hydrochloride (2) includes the following features (1) A method characterized by crystallizing a pyridazinone compound (1) in an alcohol type solvent or an alcohol type-ester type mixture solvent in the presence of hydrogen chloride and water.

(2) A method characterized by crystallizing a 2-hydrochloride of a pyridazinone compound (1) in an alcohol type solvent or an alcohol type-ester type mixture solvent in the presence of hydrogen chloride and water.

(3) A method characterized by crystallizing a 1-hydrochloride of a pyridazinone compound (1) in an alcohol type solvent or an alcohol type-ester type mixture solvent in the presence of hydrogen chloride and water.

(4) The method according to the above method (1), (2) or (3), wherein the alcohol type solvent is methanol or ethanol.

(5) The method according to the above method (1), (2) or (3), wherein the alcohol type-ester type mixture solvent is methanol-ethyl acetate mixture solvent.

(6) The method according to the above method (1), (2) or (3), wherein the alcohol type-ester type mixture solvent is ethanol-ethyl acetate mixture solvent.

Now, the method for producing the compound of the present invention is described in more details hereinafter.

A 2-hydrochloride of pyridazinone compound (1) obtained from a three component solvent system of chloroform-methanol-diethyl ether disclosed in WO95/01343 and JP-A-8-041033 can be obtained also from a two component system solvent of ethyl acetate-methanol as shown in Reference Example 2. In this case, hydrogen chloride is added in the form of a methanol solution, but if this is replaced by a solution of 35% hydrochloric acid diluted with methanol, a 3/2-hydrochloride (the compound of the present invention) can be obtained, as shown in Example 1. Thus, the presence of water plays an important role. Under this condition, even when a 2-hydrochloride is added as a seed crystal, a crystal obtained is a 3/2-hydrochloride. As concretely shown in the Examples, the 3/2-hydrochloride could be obtained even when crystallizing conditions were largely varied, and this fact proves that the 3/2-hydrochloride is not a simple mixture of 2-hydrochloride and 1-hydrochloride.

The compound (1) used as a starting material in the production method of the present invention may be a 2-hydrochloride, a 1-hydrochloride or other salts.

Examples of a solvent usable in the present invention include ethyl acetate-ethanol of Example 2 and ethanol alone of Example 3 in view of a production process of a starting material for a pharmaceutical product, but the solvent is not specially limited and other alcohol type or ester type solvents may be used. Examples of the alcohol type solvent include methanol, propanol, isopropanol, ethylene glycol or the like, and examples of the ester type solvent include methyl acetate, isopropyl acetate, ethyl propionate or the like.

An amount of a solvent used is not specially limited, but if the amount of a solvent is smaller, there is a tendency that a time required for crystallization is reduced. However, if the amount of a solvent is smaller than 1.5 times weight to the compound, stirring becomes difficult and causes a problem during mass production.

An amount of hydrogen chloride is necessary to be at least 2 mol time amount (hydrogen chloride) to the compound (1), but the upper limit amount is not specially limited. However, when taking economic conditions, operation efficiency and risk of hydrolysis of the compound into consideration, the amount of hydrogen chloride is generally in the range of from 2 time mol to 8 time mol amounts, preferably from 2.5 time mol to 4 time mol amounts. Hydrogen chloride may be used in the form of a 35% hydrochloric acid solution. As previously mentioned above, water in hydrochloric acid plays an important role in the production method of the present invention.

In order to obtain a 3/2-hydrochloride, the amount of water is preferably in the range of from 0.17 to 1 time weight to 4-chloro-5-[3-(4-benzylpiperazin-1-yl) carbonylmethoxy-4-methoxybenzylamino]-3 (2H) -pyridazinone used as a starting material. The optimum water amount varies depending on a kind and an amount of a solvent used, but concretely a 0.5 time amount is most suitable in the case of ethanol-ethyl acetate type mixture solvent. In the following Examples, 35% hydrochloric acid which is a commercially available concentrated hydrochloric acid was used, but hydrochloric acid used is not necessarily limited thereto.

As described in the following Examples, a relatively long time is required for crystallization. Therefore, such a high crystallization temperature as to cause hydrolysis of the compound after adding hydrochloric acid is not a good condition. On the other hand, if the temperature is too low, an oily material is formed, and crystallization is disturbed. Accordingly, crystallization is carried out preferably in the range of from –20° C. to 40° C., more preferably from 0° C. to 20° C.

Also, in order to reduce a time required for crystallization, it is quite useful to use a seed crystal.

BEST MODE FOR CARRYING OUT THE INVENTION

EXAMPLES

Figure 1:
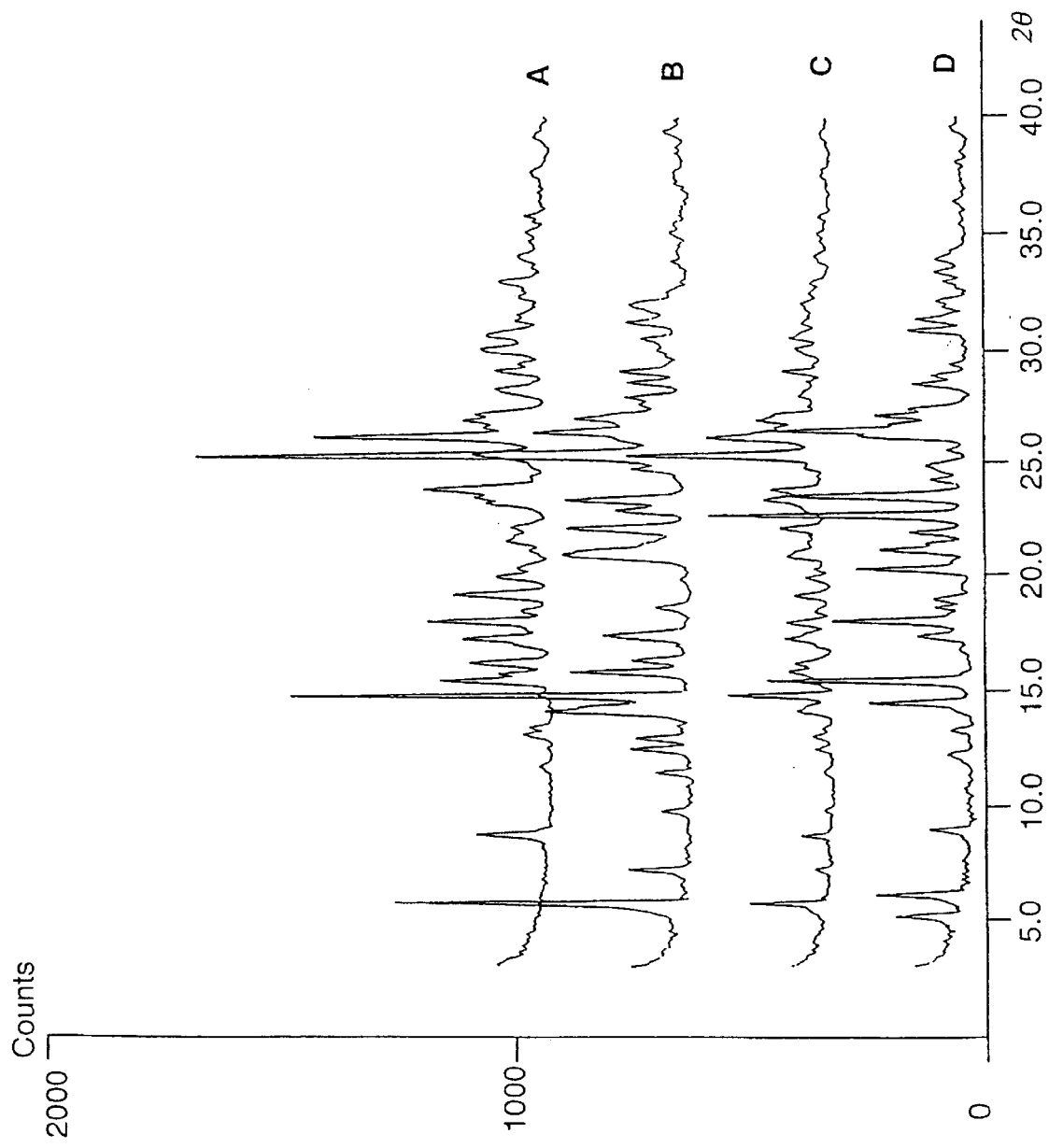
FIG. 1 shows powder X-ray diffraction data illustrating that 3/2-hydrochloride is not a simple mixture of 1-hydrochloride and 2-hydrochloride.
A: 2-hydrochloride
B: 1-hydrochloride
C: equivalent amount mixture of 1-hydrochloride and 2-hydrochloride
D: 3/2-hydrochloride

Reference Examples, Preparation Examples and Test Examples

Now, the present invention will be described in further detail with reference to Examples (Reference Examples, Preparation Examples and Test Examples), but it should be understood that the present invention is by no means restricted to such specific Examples. In the Examples, a seed crystal used is the same compound as the subject compound. Also, a 2-hydrochloride, a 3/2-hydrochloride and a 1-hydrochloride were determined by titration of chlorine ion with silver nitrate.

Test Example 1

Hygroscopic test of 2-hydrochloride and 3/2-hydrochloride under conditions of 25° C. and 75% RH A humidity conditioning solution was prepared by using a saturated aqueous solution of sodium chloride, and the solution thus prepared was placed in a humidistat, and temperature-moisture conditions at 25° C. were adjusted. 0.4 g of 2-hydrochloride and 0.2 g of 3/2-hydrochloride were weighed respectively in a weighing bottle to prepare test samples, and the test samples were subjected to hygroscopic test under the above adjusted temperature-moisture conditions to measure a water content and a decomposed material content as a lapse of time and to compare hygroscopicity and stability of the test samples.

The results (changes in water content and decomposed material as a lapse of time) of the hygroscopic test are shown in the following Table 2.

TABLE 2

| | 2-Hydrochloride | | 3/2-Hydrochloride | |
| --- | --- | --- | --- | --- |
| Time | Water content (%) | Increased decomposed material content (%) | Water content (%) | Increased decomposed material content (%) |
| 0 | 0.93 | — | 2.03 | — |
| 1 | 4.17 | 0.08 | 2.42 | 0.06 |
| 24 | 5.60 | 1.75 | 2.34 | 0.17 |
| 48 | 9.45 | 11.78 | 2.57 | 0.18 |

Test Example 2

In order to prove that 3/2-hydrochloride is not a mixture of 2-hydrochloride and 1-hydrochloride, each compound was subjected to powder X-ray diffraction measurement analysis to compare an X-ray diffraction pattern of each crystal.

The measurement method was carried out in the following manner.

1-Hydrochloride, 3/2-hydrochloride and 2-hydrochloride were subjected respectively to powder X-ray diffraction analysis. Further, a physically mixed sample prepared by mixing 1-hydrochloride and 2-hydrochloride in an equivalent amount, was subjected to X-ray diffraction analysis in the same manner as above to compare an X-ray diffraction pattern of each crystal of each compound. As this result, it was proved that the powder X-ray diffraction pattern of 3/2-hydrochloride is clearly different from that of the physically mixed sample of 1-hydrochloride and 2-hydrochloride, and it is quite evident that the 3/2-hydrochloride is not a simple mixture of 1-hydrochloride and 2-hydrochloride.

Reference Example 1

2-hydrochloride (crystallization by 3 component system of chloroform-methanol-diethyl ether)

2-Hydrochloride of 4-chloro-5-[3-(4-benzylpiperazin-1-yl) carbonylmethoxy-4-methoxybenzylamino]-3 (2H)-pyridazinone 75.0 g of 4-chloro-5-[3-(4-benzylpiperazin-1-yl) carbonylmethoxy-4-methoxybenzylamino]-3(2H)-pyridazinone was added to 300 ml of chloroform, and the mixture was heated to be dissolved. 300 ml of ethanol was added to the solution thus obtained, and 50 g of 34.5 w/w% hydrogen chloride-ethanol was further added thereto. 100 ml of chloroform, and 500 ml of diethyl ether were added to the resultant solution, and the mixture was stirred for one night at room temperature. A precipitate obtained was taken out by filtration, and was dried at 60° C. for 5 hours under reduced pressure to obtain 77.8 g of a white powder of the subject compound. Melting point: 178.3 –182.4° C.

Reference Example 2

2-Hydrochloride (crystallization by 2 component system of ethyl acetate-methanol)

2.60 g of 4-chloro-5-[3-(4-benzylpiperazin-1-yl) carbonylmethoxy-4-methoxybenzylamino]-3(2H)-pyridazinone was added to 6.51 g of methanol and 2.60 g of ethyl acetate, and was heated at an internal temperature of 45° C. to be dissolved. 7.30 g of 10 w/w% hydrogen chloride-methanol was added to the solution thus obtained. The resultant mixture was gradually cooled to 35° C., and a seed crystal was added thereto to precipitate a crystal. 8.95 g of ethyl acetate was added to this solution, and the resultant mixture was subjected to aging at room temperature for 1.5 hours and under ice-cooling condition for 2 hours. A precipitate obtained was taken out by filtration, and was dried at 60° C. for 2 hours under reduced pressure to obtain 2.41 g of a white powder of the subject compound. Melting point: 178.3 –182.4° C.

Reference Example 3

1-Hydrochloride 2.14 g of 4-chloro-5-[3-(4-benzylpiperazin-1-yl) carbonylmethoxy-4-methoxybenzylamino]-3(2H)-pyridazinone was added to 10.67 g of methanol, 4 mol/kg hydrochloric acid methanol solution and 15.20 g of ethyl acetate, and was heated to be dissolved. The resultant mixture was stirred at room temperature for 5 hours, and a precipitate obtained was taken out by filtration and was dried at 60° C. for 2 hours to obtain 2.41 g of a white powder of the subject compound. The 4 mol/kg hydrochloric acid methanol solution used was prepared from 41.7 g of 35% hydrochloric acid aqueous solution and 58.3 g of methanol. Melting point: 191.6 –196.2° C.

Example 1

3/2-hydrochloride (crystallization by 2 component system of ethyl acetate-methanol)

6.42 g of 4-chloro-5-[3-(4-benzylpiperazin-1-yl) carbonylmethoxy-4-methoxybenzylamino]-3 (2H) -pyridazinone was added to 15.21 g of methanol, and was maintained at 15° C. 3.0 g of 4 mol/kg hydrochloric acid methanol solution was added to the resultant mixture and was stirred. 6.0 g of 4 mol/kg hydrochloric acid methanol solution and 1.11 g of water were further added to the resultant mixture, and a crystal was completely dissolved. After confirming the dissolution of crystal, 130 mg of a seed crystal was added thereto, and crystallization was carried out for 1.5 hour. After the crystallization, 77.13 g of ethyl acetate was dropwise added to the resultant mixture for about 1 hour. After the dropwise addition, the mixture was cooled to 5° C. for 30 minutes, and was further cooled to 0C. for 1.5 hours. A crystal obtained was taken out by filtration, and the crystal was washed with 9 g of methanol/ethyl acetate mixture solution and was dried under reduced pressure to obtain 6.42 g of a white crystal of 3/2-hydrochloride of a pyridazinone compound having the formula (2). The 4 mol/kg hydrochloric acid methanol solution used was prepared from 41.7 g of 35% hydrochloric acid aqueous solution and 58.3 g of methanol. Melting point: 167.6 –172.0° C.

Experiments carried out under such conditions as shown in the following Table 3 are illustrated as Examples. Compound (1) was used as a starting material. The amount of a solvent was expressed by times by weight to the starting material, and the amount of hydrogen chloride was expressed by mols to the starting material, and the amount of a seed crystal was expressed by wt% to the starting material.

TABLE 3

| Items | No. | Temp. (° C.) | EtOH (times) | Water (times) | Hydrogen chloride (equivalent) | Seed crystal (wt %) | Aging time (hrs) | Solvent added Kind | Solvent added Amount (times) | Yield (%) |
|---|---|---|---|---|---|---|---|---|---|---|
| Solvent amount | 1 | 15 | 1 | 0.25 | 3 | 2 | 1.2 | EtOH | 10 | 90.0 |
|  | 2 |  | 2 | 0.5 |  |  | 5 | AcOEt | 10 | 92.3 |
| Temperature | 3 | 10 | 2 | 0.5 | 2.5 | 2 | 14 | AcOEt | 10 | 77.4 |
|  | 2 | 15 |  |  |  |  | 5 |  | 10 | 92.3 |
|  | 4 | 20 |  |  |  |  | 4 |  |  | 91.9 |
|  | 5 | 20 |  |  |  |  | 4 |  |  | 91.9 |
|  | 6 | 30 |  |  |  |  | 2 |  | 7 | 88.9 |
|  | 7 | 40 |  |  |  |  | 1.5 |  |  | 79.6 |
| Hydrogen chloride | 8 | 15 | 2 | 0.5 | 1.8 | 2 | 14 | AcOEt | 10 | 79.2 |
|  | 9 |  |  |  | 2 |  | 14 |  |  | 91.0 |
|  | 10 |  |  |  | 2.5 |  | 9.5 |  |  | 95.0 |
|  | 2 |  |  |  | 3 |  | 5 |  |  | 92.3 |
|  | 11 |  |  |  | 4 |  | 3.5 |  |  | 97.5 |
|  | 12 |  |  |  | 6 |  | 2.5 |  |  | 95.9 |
| Seed crystal | 13 | 15 | 2 | 0.5 | 3 | 10 | 2.5 | AcOEt | 10 | 91.8 |
|  | 14 | 16–17.5 |  |  |  | 4 | 6 |  | 7 | 94.4 |
|  | 15 | 16–17.5 |  |  |  | 2 | 7 |  | 10 | 94.9 |
| Water | 2 | 15 | 2.0 | 0.5 | 3 | 2 | 5 | AcOEt | 10 | 92.3 |
|  | 16 |  | 1.6 | 0.5 |  |  | 4.5 |  | 10 | 95.2 |
|  | 17 |  | 1.94 | 0.6 |  |  | 9 |  | 7 | 88.7 |
|  | 18 |  | 2.2 | 0.5 |  |  | 8 |  | 10 | 94.1 |

Example 2

3/2-Hydrochloride (crystallization by 2 component system of ethyl acetate-ethanol)

4.3 g of ethanol, 1.08 g of water and 2.15 g of 4-chloro-5-[3-(4-benzylpiperazin-1-yl)carbonylmethoxy-4-methoxybenzylamino]-3(2H)-pyridazinone were maintained at 30° C., and 1.0 g of 4 mol/kg hydrochloric acid ethanol solution was added thereto, and the resultant mixture was stirred until being dissolved. The temperature of this solution was adjusted to 15° C., and 2.0 g of 4 mol/kg hydrochloric acid ethanol solution was added thereto, and 40 mg of a seed crystal was further added thereto, and crystallization was carried out for 5 hours. After the crystallization, 21.5 g of ethyl acetate was dropwise added thereto for about 1 hour. After the dropwise addition, a mixture was cooled to 5° C. for 30 minutes, and was further cooled to 0° C. for 1.5 hours. A crystal obtained was taken out by filtration, and the crystal was washed with a small amount of ethanol/ethyl acetate mixture solution, and was dried under reduced pressure to obtain 2.04 g of a white crystal of 3/2-hydrochloride of a pyridazinone compound having the formula (2). The 4 mol/kg hydrochloric acid ethanol solution used was prepared from 41.7 g of 35% hydrochloric acid aqueous solution and 58.3 g of ethanol. Melting point: 167.6 –172.0° C.

Example 3

3/2-Hydrochloride (crystallization by ethanol alone)

A mixture solution of 4.3 g of ethanol, 2.0 g of 4 mol/kg hydrochloric acid ethanol solution and 1.08 g of water was maintained at 15° C., and 2.15 g (4 mmol) of 4-chloro-5-[3-(4-benzylpiperazin-1-yl) carbonylmethoxy-4-methoxybenzylamino]-3(2H)-pyridazinone was gradually added thereto and was dissolved. 40 mg of a seed crystal was added to the resultant solution, and crystallization was carried out at 15° C. for 14 hours. After the crystallization, 21.5 g of ethanol was dropwise added thereto for about 1 hour. After the dropwise addition, the mixture was cooled to 5° C. for 30 minutes, and was further cooled to 0° C. for 1.5 hours. A crystal obtained was taken out by filtration, and the crystal was washed with a small amount of ethanol and was dried under reduced pressure to obtain 1.84 g of a white crystal of 3/2-hydrochloride of a pyridazinone compound having the formula (2). Melting point: 167.6 –172.0° C.

INDUSTRIAL APPLICABILITY

3/2-Hydrochloride of 4-chloro-5-[3-(4-benzylpiperazin-1-yl) carbonylmethoxy-4-methoxybenzylamino]-3 (2H)-pyridazinone of the present invention is a compound excellent in hygroscopicity and stability which is useful as a pharmaceutical product having a bronchodilation function, an antiallergy function and an antiplatelet function.

What is claimed is:

1. 3/2-Hydrochloride of 4-chloro-5-[3-(4-benzylpiperazin-1-yl)carbonylmethoxy-4-methoxybenzylamino]-3(2H)-pyridazinone.

2. A method for producing the compound claimed in claim 1, which comprises crystallizing 4-chloro-5-[3-(4-benzylpiperazin-1-yl) carbonylmethoxy-4-methoxybenzylamino]-3(2H)-pyridazinone in an alcohol type solvent or an alcohol type-ester type mixture solvent in the presence of hydrogen chloride and water.

3. A method for producing the compound claimed in claim 1, which comprises crystallizing 2-hydrochloride of 4-chloro-5-[3-(4-benzylpiperazin-1-yl)carbonylmethoxy-4-methoxybenzylamino]-3(2H)-pyridazinone in an alcohol type solvent or an alcohol type-ester type mixture solvent in the presence of hydrogen chloride and water.

4. A method for producing the compound claimed in claim 1, which comprises crystallizing 1-hydrochloride of 4-chloro-5-[3-(4-benzylpiperazin-1-yl) carbonylmethoxy-4-methoxybenzylamino]-3(2H)-pyridazinone in an alcohol type solvent or an alcohol type-ester type mixture solvent in the presence of hydrogen chloride and water.

5. The method according to claim 2, wherein the alcohol type solvent is methanol or ethanol.

6. The method according to claim 2, wherein the alcohol type-ester type mixture solvent is a methanol-ethyl acetate mixture solvent.

7. The method according to claim 2, wherein the alcohol type-ester type mixture solvent is an ethanol-ethylacetate mixture solvent.

8. A pharmaceutical composition comprising the 3/2-Hydrochloride of claim 1 and a pharmaceutically acceptable carrier.

9. The method according to claim 3, wherein the alcohol type solvent is methanol or ethanol.

10. The method according to claim 4, wherein the alcohol type solvent is methanol or ethanol.

11. The method according to claim 3, wherein the alcohol type-ester mixture solvent is a methanol-ethyl acetate mixture solvent.

12. The method according to claim 4, wherein the alcohol type-ester mixture solvent is a methanol-ethyl acetate mixture solvent.

13. The method according to claim 3, wherein the alcohol type-ester mixture solvent is an ethanol-ethyl acetate mixture solvent.

* * * * *